United States Patent [19]

Effland et al.

[11] Patent Number: 5,214,058
[45] Date of Patent: May 25, 1993

[54] 1-(PYRIDINYLALKYL)-1H-INDOLES, INDOLINES AND RELATED ANALOGS

[75] Inventors: Richard C. Effland, Bridgewater; Larry Davis, Sergeantsville; Gordon E. Olsen, Somerset, all of N.J.

[73] Assignee: Hoechst-Roussel Pharmaceuticals Inc., Somerville, N.J.

[21] Appl. No.: 722,465

[22] Filed: Jun. 27, 1991

Related U.S. Application Data

[63] Continuation-in-part of Ser. No. 566,575, Aug. 13, 1990, abandoned.

[51] Int. Cl.$^5$ .................... C07D 401/06; A61K 31/44
[52] U.S. Cl. ...................................... 514/339; 546/273
[58] Field of Search ........................ 546/273; 514/339

[56]  References Cited

U.S. PATENT DOCUMENTS 4,880,822  11/1989  Effland et al. ...................... 514/339

FOREIGN PATENT DOCUMENTS 2102795  2/1983  United Kingdom .

OTHER PUBLICATIONS

CA: 109:150001j—Tet. Letters, 1987-28(48), pp. 6077-6080.
J. Bosch et al., Mercuric Acetate Cyclization of 4-(Pyrrolymethyl and 4-(Indolymethyl)piperidines to Bridged Polycyclic Systems, J. Org. Chem. 48, 25 (1983) 4836-41.
C. W. Whitehead et al., Effect of Lipophilic Substituents on Some Biological Properties of Indoles, J. Med. Chem. 17, 12 (1974), 129 1304.
Bosch et al., Synthetic Studies on the Indole Alkaloid Vinoxine, 51, 12, (1986), 2289-97.
J. Bosch et al., Model Studies in the Vinoxine Series, Heterocycles, 19, 5 (1982), 853-56.
M. L. Bennasar et al., Synthetic Applications of 2-Cyanopiperidines, Tetrahedron, 42, 2 (1986), 637-47.
CA 70:19857b Sheinkman et al.

Primary Examiner—Jane T. Fan
Attorney, Agent, or Firm—Elliott Korsen

[57]  ABSTRACT

This invention relates to compounds of the formula

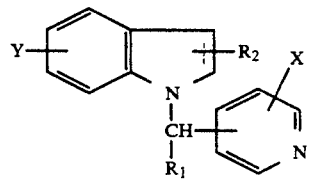

wherein
 $R_1$ is hydrogen, loweralkyl, arylloweralkyl, loweralkenyl or loweralkynyl;
 $R_2$ is hydrogen, loweralkyl, loweralkenyl, formyl or cyano;
 X is hydrogen, halogen, nitro, amino, loweralkyl, loweralkoxy or hydroxy;
 Y is hydrogen, loweralkyl, loweralkoxy, arylloweralkoxy, hydroxy, halogen, nitro or amino, with the proviso that when Y is hydrogen or loweralkyl, $R_1$ is not hydrogen and $R_2$ is not formyl; a pharmaceutically acceptable acid addition salt thereof, or where applicable, a geometric or optical isomer or racemic mixture thereof. The compounds of the invention are useful for the treatment of various memory dysfunctions characterized by a decreased cholinergic function, such as found in Alzheimer's disease and other senile dementia.

13 Claims, No Drawings

1-(PYRIDINYLALKYL)-1H-INDOLES, INDOLINES AND RELATED ANALOGS

This application is a continuation-in-part application of U.S. patent application Ser. No. 566,575 filed Aug. 13, 1990, abandoned.

This invention relates to compounds of the formula

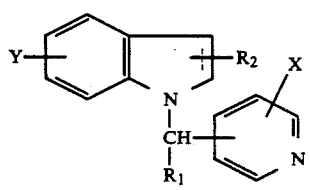

(I)

wherein $R_1$ is hydrogen, loweralkyl, arylloweralkyl, loweralkenyl or loweralkynyl;

$R_2$ is hydrogen, loweralkyl, loweralkenyl, formyl or cyano;

X is hydrogen, halogen, nitro, amino, loweralkyl, loweralkoxy or hydroxy;

Y is hydrogen, loweralkyl, loweralkoxy, arylloweralkoxy, hydroxy, halogen, nitro or amino, with the proviso that when Y is hydrogen or loweralkyl, $R_1$ is not hydrogen and $R_2$ is not formyl; a pharmaceutically acceptable acid addition salt thereof, or where applicable, a geometric or optical isomer or racemic mixture thereof. The compounds of the invention are useful for the treatment of various memory dysfunctions characterized by a decreased cholinergic function, such as found in Alzheimer's disease and other senile dementia.

The dotted lines present in Formula (I) signify an optional double bond. When the double bond is present, the formula (I) compounds represented are indoles.

Throughout the specification and appended claims, a given chemical formula or name shall encompass all geometrical and optical isomers and racemic mixtures where such isomers and mixtures exist.

Unless otherwise stated or indicated, the following definitions shall apply throughout the specification and the appended claims.

The term "loweralkyl" refers to a straight or branched chain hydrocarbon having from 1 to 6 carbon atoms, e.g., methyl, ethyl, propyl, isopropyl, n-butyl, neopentyl, n-hexyl, etc.

The term "aryl" refers to a phenyl group optionally monosubstituted or disubstituted with a loweralkyl, loweralkoxy, halogen or trifluoromethyl group.

The term "alkoxy" refers to a monovalent substituent which consists of an alkyl group linked through an ether oxygen having its free valence bond from the ether oxygen; e.g., methoxy, ethoxy, propoxy, butoxy, etc.

The term "alkenyl" refers to acyclic hydrocarbons with one double bond of the general formula $C_nH_{2n}$, e.g., ethylene, butylene, etc.

The term "alkynyl" refers to acyclic hydrocarbons with one triple bond of the general formula $C_nH_{2n-2}$, e.g., acetylene, butyne, etc.

The term "halogen" refers to a member of the halogen family consisting of fluorine, chlorine, bromine and iodine.

The compounds of this invention are prepared in the following manner. The substituents $R_1$, $R_2$, X and Y are as defined above unless otherwise indicated.

Compound II of the formula

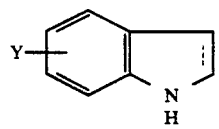

(II)

is reacted with a haloalkylpyridine hydrochloride of the formula

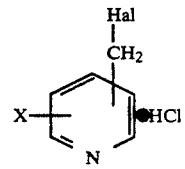

where Hal is halogen, to afford Compound III of the formula

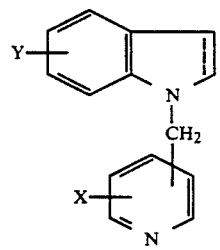

(III)

This reaction typically takes place in the presence of a base such as potassium hydroxide and a suitable solvent such as dimethylsulfoxide (DMSO) or dimethylformamide at ambient temperature to 50° C. for 1 to 20 hours.

Compound III, where Y is phenylmethoxy, is hydrogenated in a routine manner, for instance, using a noble metal catalyst under a hydrogen atmosphere, to afford Compound IV of the formula

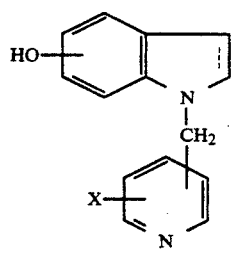

(IV)

The noble metal catalyst is selected from palladium or platinum on carbon. The reaction typically takes place at a temperature of about 20° C. to 70° C. for 1 to 20 hours.

Compound III may be reacted with n-butyllithium and a loweralkyl halide of the formula $R_1$-Hal, where $R_1$ is as previously defined and Hal is chlorine or bromine, in a suitable solvent to afford compound IIIa of the formula

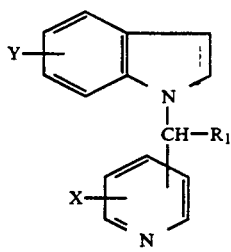

(IIIa)

Typically, this reaction takes place in tetrahydrofuran or ether at a temperature of about −80° to 0° C. for 1 to 8 hours.

Compound IIIa, where Y is phenylmethoxy, is subsequently hydrogenated in a manner similar to that described above to afford Compound IV, where $R_1 \neq$ hydrogen.

The compounds of formula I of the present invention are useful in the treatment of various memory dysfunctions characterized by decreased cholinergic function, such as found in Alzheimer's disease. This utility is manifested by the ability of these compounds to inhibit the enzyme acetylcholinesterase and thereby increase acetylcholine levels in the brain.

Cholinesterase Inhibition Assay

Cholinesterases are found throughout the body, both in the brain and in serum. However, only brain acetylcholinesterase (AChE) distribution is correlated with central cholinergic innervation. This same innervation is suggested to be weakened in Alzheimer patients. We have determined in vitro inhibition of acetylcholinesterase activity in rat striatum according to the method described below.

In Vitro Inhibition of Acetylcholinesterase Activity in Rat Striatum

Acetylcholinesterase (AChE), which is sometimes called true or specific cholinesterase, is found in nerve cells, skeletal muscle, smooth muscle, various glands and red blood cells. AChE may be distinguished from other cholinesterases by substrate and inhibitor specificities and by regional distribution. Its distribution in the brain correlates with cholinergic innervation and subfractionation shows the highest level in nerve terminals.

It is generally accepted that the physiological role of AChE is the rapid hydrolysis and inactivation of acetylcholine. Inhibitors of AChE show marked cholinomimetic effects in cholinergically-innervated effector organs and have been used therapeutically in the treatment of glaucoma, myasthenia gravis and paralytic ileus. However, recent studies have suggested that AChE inhibitors may also be beneficial in the treatment of Alzheimer's dementia.

The method described below was used in this invention for assaying anticholinesterase activity. This is a modification of the method of Ellman et al., Biochem. Pharmacol. 7, 88 (1961).

Procedure

A. Reagents
  1. 0.05M Phosphate buffer, pH 7.2
    (a) 6.85 g $NaH_2PO_4 \cdot H_2O$/100 ml distilled $H_2O$
    (b) 13.40 g $Na_2HPO_4 \cdot 7H_2O$/100 ml distilled $H_2O$
    (c) add (a) to (b) until pH reaches 7.2
    (d) Dilute 1:10
  2. Substrate in buffer
    (a) 198 mg acetylthiocholine chloride (10 mM)
    (b) q.s. to 100 ml with 0.05M phosphate buffer, pH 7.2 (reagent 1)
  3. DTNB in buffer
    (a) 19.8 mg 5,5-dithiobisnitrobenzoic acid (DTNB) (0.5 mM)
    (b) q.s. to 100 ml with 0.05M phosphate buffer, pH 7.2 (reagent 1)
  4. A 2 mM stock solution of the test drug is made up in a suitable solvent and q.s. to volume with 0.5 mM DTNB (reagent 3). Drugs are serially diluted (1:10) such that the final concentration (in cuvette) is $10^{-4}M$ and screened for activity. If active, $IC_{50}$ values are determined from the inhibitory activity of subsequent concentrations.

B. Tissue Preparation

Male Wistar rats are decapitated, brains rapidly removed, corpora striata dissected free, weighed and homogenized in 19 volumes (approximately 7 mg protein/ml) of 0.05M phosphate buffer, pH 7.2, using a Potter-Elvehjem homogenizer. A 25 microliter aliquot of the homogenate is added to 1 ml of vehicle or various concentrations of the test drug and preincubated for 10 minutes at 37° C.

C. Assay

Enzyme activity is measured with the Beckman DU-50 spectrophotometer. This method can be used for $IC_{50}$ determinations and for measuring kinetic constants.

Instrument Settings

Kinetics Soft-Pac Module #598273 (10)
Program #6 Kindata:
Source—Vis
Wavelength—412 nm
Sipper—none
Cuvettes—2 ml cuvettes using auto 6-sampler
Blank—1 for each substrate concentration
Interval time—15 seconds (15 or 30 seconds for kinetics)
Total time—5 minutes (5 or 10 minutes for kinetics)
Plot—yes
Span—autoscale
Slope—increasing
Results—yes (gives slope)
Factor—1

Reagents are added to the blank and sample cuvettes as follows:

| | |
|---|---|
| Blank: | 0.8 ml Phosphate Buffer/DTNB |
| | 0.8 ml Buffer/Substrate |
| Control: | 0.8 ml Phosphate Buffer/DTNB/Enzyme |
| | 0.8 ml Phosphate Buffer/Substrate |
| Drug: | 0.8 ml Phosphate Buffer/DTNB/Drug/Enzyme |
| | 0.8 ml Phosphate Buffer/Substrate |

Blank values are determined for each run to control non-enzymatic hydrolysis of substrate and these values are automatically substracted by the kindata program available on kinetics soft-pac module. This program also calculates the rate of absorbance change for each cuvette.

For $IC_{50}$ Determinations

Substrate concentration is 10 mM diluted 1:2 in assay yielding final concentration of 5 mM. DTNB concentration is 0.5 mM yielding 0.25 mM final concentration $$\% \text{ Inhibition} = \frac{\text{slope control} - \text{slope drug}}{\text{slope control}} \times 100$$

Results of this assay for representative compounds of this invention and eseroline (reference) are presented in Table 1.

TABLE 1

| Inhibition of Brain Acetylcholinesterase Activity | |
|---|---|
| Compound | % Inhibition @ Dose |
| 1-(4-pyridinylmethyl)-1H-indol-5-ol | 24% @ 100 μM |
| Eseroline (Reference Compound) | 50% @ 6.4 μM |

This utility is further demonstrated by the ability of these compounds to restore cholinergically deficient memory in the Dark Avoidance Assay described below.

Dark Avoidance Assay

In this assay mice are tested for their ability to remember an unpleasant stimulus for a period of 24 hours. A mouse is placed in a chamber that contains a dark compartment; a strong incandescent light drives it to the dark compartment, where an electric shock is administered through metal plates on the floor. The animal is removed from the testing apparatus and tested again, 24 hours later, for the ability to remember the electric shock.

If scopolamine, an anticholinergic that is known to cause memory impairment, is administered before an animal's initial exposure to the test chamber, the animal re-enters the dark compartment shortly after being placed in the test chamber 24 hours later. This effect of scopolamine is blocked by an active test compound, resulting in a greater interval before re-entry into the dark compartment.

The results for an active compound are expressed as the percent of a group of animals in which the effect of scopolamine is blocked, as manifested by an increased interval between being placed in the test chamber and re-entering the dark compartment.

Results of this assay for representative compounds of this invention and those for tacrine and pilocarpine (reference compounds) are presented in Table 2.

TABLE 2

| Compound | Dose (mg/kg of body weight, s.c.) | % of Animals with Scopolamine-Induced Memory Deficit Reversal |
|---|---|---|
| 1-[1-(4-pyridinyl)-butyl]-1H-indole | 0.3 | 20 |
| 1-(4-pyridinylmethyl)-1H-indole | 0.3 | 33 |
|  | 1.0 | 20 |
| Tacrine | 0.63 | 13 |
| Pilocarpine | 5.0 | 13 |

Effective quantities of the compounds of the present invention may be administered to a subject by any one of various methods, for example, orally as in capsules or tablets, parenterally in the form of sterile solutions or suspensions, and in some cases intravenously in the form of sterile solutions. The compounds of the present invention, while effective themselves, may be formulated and administered in the form of their pharmaceutically acceptable addition salts for purposes of stability, convenience of crystallization, increased solubility and the like.

Preferred pharmaceutically acceptable addition salts include salts of inorganic acids such as hydrochloric, hydrobromic, sulfuric, nitric, phosphoric and perchloric acids; as well as organic acids such as tartaric, citric, acetic, succinic, maleic, fumaric, and oxalic acids.

The active compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 75% of the weight of the unit. The amount of compound present in such composition is such that a suitable dosage will be obtained. Preferred compositions and preparations according to the present invention are prepared so that an oral dosage unit form contains between 1.0–300 mgs of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel ™, corn starch and the like; a lubricant such as magnesium stearate or Sterotex ®; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of the aforesaid compound, but may be varied between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 mgs of active compound.

The solutions or suspensions may also include the following components; a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

Examples of the compounds of the invention are listed below:

5-phenylmethoxy-1-(4-pyridinylmethyl)-1H-indole;
1-(4-pyridinylmethyl)-1H-indol-5-ol;
1-[1-(4-pyridinyl)butyl]-1H-indole;
1-(4-pyridinylmethyl)-1H-indole;
5-phenylmethoxy-1-[1-(4-pyridinylbutyl)]-1H-indole;
1-[1-(4-pyridinylbutyl)]-1H-indol-5-ol;
[1-(4-pyridinylbutyl)]-5-methoxy-1H-indole;
1-[1-(3-methoxy-4-pyridinyl)butyl]-1H-indole;
1-[1-(3-fluoro-4-pyridinyl)butyl]-1H-indole;
1-[1-(3-fluoro-4-pyridinyl)butyl]-5-phenylmethoxy-1H-indole;
5-chloro-1-(4-pyridinylmethyl)-1H-indole;
5-methyl-1-[1-(4-pyridinyl)butyl]-1H-indole;
3-methyl-5-phenylmethoxy-1-[1-(4-pyridinylbutyl)]-1H-indole;
1-[1-(3-fluoro-4-pyridinyl)butyl]-3-methyl-5-phenylmethoxy-1H-indole;
2,3-dihydro-1-(4-pyridinylmethyl)-1H-indole;
2,3-dihydro-1-[1-(4-pyridinyl)butyl]-1H-indole;
2,3-dihydro-5-phenylmethoxy-1-(4-pyridinylmethyl)-1H-indole;
2,3-dihydro-5-fluoro-1-[1-(4-pyridinyl)butyl]-1H-indole;
2,3-dihydro-1-[1-(3-fluoro-4-pyridinyl)butyl]-5-methoxy-1H-indole; and
2,3-dihydro-3-methyl-1-(4-pyridinylmethyl)-1H-indole.

The following examples are for illustrative purposes and are not to be construed as limiting the invention disclosed herein. All temperatures are given in degrees centigrade (°C.) unless indicated otherwise.

EXAMPLE 1

5-Phenylmethoxy-1-(4-pyridinylmethyl)-1H-indole

To a solution of 5-phenylmethoxy-1H-indole (22.6 g) in 130 ml dimethylsulfoxide, was added milled potassium hydroxide (18 g) and the mixture was stirred at ambient temperature for two hours. The mixture was cooled with an ice bath, then 4-chloromethylpyridine hydrochloride (16.4 g) was added portionwise over a period of fifteen minutes. After stirring at ambient temperature for four hours, the mixture was poured into two liters ice water and stirred for ten minutes. The resultant precipitate was collected, washed with water and dissolved in ethyl acetate. The organic layer was washed with water and saturated sodium chloride and dried over anhydrous magnesium sulfate.

After filtering, the solution was evaporated to afford a solid, (~30 g) which was triturated with ether, collected and dried to give 27 g of a solid, m.p. 123°-125° C. A sample of this material was eluted on a silica gel column with ethyl acetate/dichloromethane (1:2) via high pressure liquid chromatography (HPLC). The desired fractions were combined to yield 5-phenylmethoxy-1-(4-pyridinylmethyl)-1H-indole, as a solid, m.p. 124°-5° C.

| Analysis: | | | |
|---|---|---|---|
| Calculated for C$_{21}$H$_{18}$N$_2$O: | 80.23% C | 5.77% H | 8.91% N |
| Found: | 79.92% C | 5.41% H | 8.79% N |

EXAMPLE 2

1-(4-Pyridinylmethyl)-1H-indol-5-ol

To a suspension of 10% Pd/C (1.5 g) in 50 ml ethanol in a 500 ml Parr hydrogenation bottle, was added a suspension of 5-phenylmethoxy-1-(4-pyridinylmethyl)-1H-indole in 200 ml ethanol. The mixture was shaken at 50° C. under 50 psi hydrogen for one hour, then cooled, filtered, and the filtrate evaporated to a solid, 10 g, dec. 178° C. A sample of this material was eluted on a silica gel column with 2% methanol/dichloromethane via HPLC. The desired fractions were combined and evaporated to yield 2.3 g of 1-(4-pyridinylmethyl)-1H-indol-5-ol, as a solid, m.p. 185°-186° C.

| Analysis: | | | |
|---|---|---|---|
| Calculated for C$_{14}$H$_{12}$N$_2$O: | 74.98% C | 5.40% H | 12.49% N |
| Found: | 74.76% C | 5.46% H | 12.34% N |

EXAMPLE 3

1-(4-Pyridinylmethyl)-1H-indole

To KOH (34 g) in 200 ml of DMSO was added indole (20 g), portionwise, and this mixture was stirred for 90 minutes at room temperature. 4-Chloromethylpyridine hydrochloride (10 g) was added portionwise, and the mixture was stirred for four hours at room temperature. The mixture was then poured into water and extracted with ether four times. The organics were combined and washed with 2N HCl. The acidic aqueous phase was then basified with NH$_4$OH and extracted with ether three times. The organics were combined and washed with NaCl and dried (anhy. MgSO$_4$). After filtering, the solvent was evaporated to yield an oil (14.5 g), which was eluted with 50% ethyl acetate/dichloromethane on a silica gel column via HPLC. The desired fractions were evaporated to yield 10.5 g of 1-(4-pyridinylmethyl)-1H-indole, as a solid, m.p. 65°-68° C.

| Analysis: | | | |
|---|---|---|---|
| Calculated for C$_{14}$H$_{12}$N$_2$: | 80.74% C | 5.81% H | 13.45% N |
| Found: | 80.59% C | 5.87% H | 13.45% N |

EXAMPLE 4

1-[1-(4-Pyridinyl)butyl]-1H-indole

To a solution of 1-(4-pyridinylmethyl)-1H-indole (4.0 g) in 100 ml of THF cooled to −78° C. was added n-butyllithium (7.6 ml) dropwise, and the mixture was stirred for 45 minutes. 1-Bromopropane (2.34 g) was added dropwise, and the mixture was stirred for 3.5 hours, allowing the temperature to rise to 0° C. The mixture was quenched with water and extracted with ethyl acetate. The organic layer was washed with water and dried (sat. NaCl, anhy. MgSO$_4$). After filtering, the solvent was evaporated to yield an oil (3.8 g) which was eluted with 50% ethyl acetate/dichloromethane on a silica gel column via HPLC. The desired fractions were evaporated to yield 2.65 g of 1-[1-(4-pyridinyl)butyl]-1H-indole, as a solid, m.p. 91°-94° C.

| Analysis: | | | |
|---|---|---|---|
| Calculated for C$_{17}$H$_{18}$N$_2$: | 81.56% C | 7.25% H | 11.19% N |
| Found: | 81.66% C | 7.32% H | 11.22% N |

EXAMPLE 5

5-Phenylmethoxy-1-[1-(4-pyridinylbutyl)]-1H-indole oxalate

To a solution of 5-phenylmethoxy-1-(4-pyridinylmethyl)-1H-indole (11.4 g) in 120 ml tetrahydrofuran at −78° C., was added n-butyllithium (2.5M solution in hexane, 14.4 ml) and the solution was stirred at −78° C. for one hour. 1-Bromopropane (30 ml) was added to the solution and the mixture was allowed to warm to ambient temperature over a period of two hours. The mixture was poured into 300 ml water, stirred for five minutes and extracted twice with ethyl acetate. The organic layer was washed with water and dried (saturated NaCl solution, anhydrous $MgSO_4$). After filtering, the solvent was evaporated to an oil, (13.5 g) which was eluted on a silica gel column with ethyl acetate/dichloromethane (1:2) via HPLC. The desired fractions were combined and evaporated to give 8.2 g an oil. A 1.0 g aliquot of this oil was dissolved in 10 ml methanol, and a solution of oxalic acid (0.3 g) in 5 ml methanol was added. The solution was diluted with 150 ml ether and the resultant precipitate was collected and dried to give 1.2 g of 5-phenylmethoxy-1-[1-(4-pyridinylbutyl)]-1H-indole oxalate, m.p. 148°–149° C.

| Analysis: | | | |
|---|---|---|---|
| Calculated for $C_{24}H_{24}N_2O \cdot C_2H_2O_4$: | 69.94% C | 5.87% H | 6.28% N |
| Found: | 70.09% C | 5.83% H | 6.22% N |

EXAMPLE 6

1-[1-(4-Pyridinylbutyl)]-1H-indol-5-ol

To a suspension of 1.0 g of 10% Pd/C in 50 ml ethanol, was added a solution of 5-phenylmethoxy-1-[1-(4-pyridinylbutyl)]-1H-indole (7.2 g) in 200 ml ethanol. After shaking under 50 psi hydrogen at 50° C. for one hour, the mixture was filtered, then evaporated to a solid, which was tritured with hexanes to give 5.0 g of 1-[1-(4-pyridinylbutyl)]-1H-indol-5-ol, m.p. 73°–75° C.

| Analysis: | | | |
|---|---|---|---|
| Calculated for $C_{17}H_{18}N_2O$: | 76.66% C | 6.81% H | 10.52% N |
| Found: | 76.23% C | 6.86% H | 10.13% N |

We claim:

1. A compound of the formula

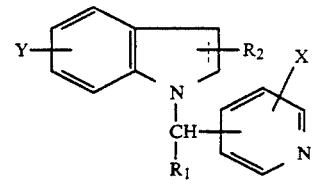

wherein
$R_1$ is hydrogen, loweralkyl, arylloweralkyl, loweralkenyl or loweralkynyl;
$R_2$ is hydrogen, loweralkyl, loweralkenyl, formyl or cyano;
X is hydrogen, halogen, nitro, amino, loweralkyl, loweralkoxy or hydroxy;
Y is loweralkoxy, arylloweralkoxy, hydroxy, halogen, nitro or amino;
the term aryl in each occurrence signifying a phenyl group optionally monosubstituted or disubstituted with a loweralkyl, loweralkoxy, halogen or trifluoromethyl group; a pharmaceutically acceptable acid addition salt thereof, or where applicable, a geometric or optical isomer or racemic mixture thereof.

2. The compound as defined in claim 1 which is 5-phenylmethoxy-1-(4-pyridinylmethyl)-1H-indole.

3. The compound as defined in claim 1 which is 1-(4-pyridinylmethyl)-1H-indol-5ol.

4. The compound as defined in claim 1 which is 5-phenylmethoxy-1-[1-(4-pyridinylbutyl)]-1H-indole.

5. The compound as defined in claim 1 which is 1-[1-(4-pyridinylbutyl)]-1H-indol-5-ol.

6. The compound as defined in claim 1 which is [1-(4-pyridinylbutyl)]-5-methoxy-1H-indole.

7. The compound as defined in claim 1 which is 1-[1-(3-methoxy-4-pyridinyl)butyl]-1H-indole.

8. The compound as defined in claim 1 which is 1-[1-(3-fluoro-4-pyridinyl)butyl]-1H-indole.

9. The compound as defined in claim 1 which is 1-[1-(3-fluoro-4-pyridinyl)butyl]-5-phenylmethoxy-1H-indole.

10. The compound as defined in claim 1 which is 3-methyl-5-phenylmethoxy-1-[1-(4-pyridinylbutyl)]-1H-indole.

11. The compound as defined in claim 1 which is 1-[1-(3-fluoro-4-pyridinyl)butyl]-3-methyl-5-phenylmethoxy-1H-indole.

12. The compound as defined in claim 1 which is 2,3-dihydro-1-[1-(3-fluoro-4-pyridinyl)butyl]-5-methoxy-1H-in dole.

13. A pharmaceutical composition which comprises an effective amount of a compound as defined in claim 1 and a pharmaceutically acceptable carrier therefor.

* * * * *